(12) United States Patent
Bermejo Osés et al.

(10) Patent No.: US 8,080,690 B2
(45) Date of Patent: Dec. 20, 2011

(54) FRAGRANCE PRECURSOR

(75) Inventors: Maria José Bermejo Osés, Barberà del Vallès (ES); Marc Arderiu Girame, Barberà del Vallès (ES); Hiroshi Abe, Barberà del Vallès (ES)

(73) Assignee: Kao Corporation S.A., Barbera del Valles (ES)

( * ) Notice: Subject to any disclaimer, the term of this patent is extended or adjusted under 35 U.S.C. 154(b) by 0 days.

(21) Appl. No.: 12/301,452

(22) PCT Filed: Mar. 29, 2007

(86) PCT No.: PCT/EP2007/002816
§ 371 (c)(1),
(2), (4) Date: Nov. 25, 2008

(87) PCT Pub. No.: WO2007/134666
PCT Pub. Date: Nov. 29, 2007

(65) Prior Publication Data
US 2009/0269294 A1    Oct. 29, 2009

(30) Foreign Application Priority Data

May 19, 2006   (EP) .................................. 06380122

(51) Int. Cl.
*C07C 217/28*   (2006.01)
(52) U.S. Cl. ...... 564/505; 564/504; 510/524; 424/70.17
(58) Field of Classification Search .................. 564/504, 564/505; 510/524
See application file for complete search history.

(56) References Cited

U.S. PATENT DOCUMENTS 6,277,796 B1    8/2001  Sivik et al.
2004/0102357 A1*  5/2004  Smith et al. .................. 512/3

FOREIGN PATENT DOCUMENTS

WO    WO 98/06803 A    2/1998
WO    WO 2004/047788 A2   6/2004

* cited by examiner

*Primary Examiner* — Brian J Davis
(74) *Attorney, Agent, or Firm* — LaRiviere, Grubman & Payne, LLP (57) ABSTRACT

The invention relates to a compound of the following formula (I) X—CR$_1$R$_2$R$_3$ wherein —R$_1$ is an organic moiety having 6 to 24 carbon atoms; —R$_2$ is H or an organic moiety having 6 to 24 carbon atoms; —R$_3$ is X or OH; —X is a moiety of the following formula (II): or an ammonium or C$_1$-C$_4$ alkyl ammonium salt of the moiety of formula (II); wherein -x is 0 or 1; -y is 0 or 1; -z is 0 or 1; -m is a number from 2 to 10; -n is a number from 0 to 10; -o is a number from 0 to 10; —R$_4$ is H or a C$_1$-C$_4$ alkyl group; —R$_5$ is a C$_6$-C$_{22}$ alkyl or alkenyl group or, if n or o is at least 1, a C$_7$-C$_{23}$ acyl group; —R$_6$ is H or R$_5$; —R$_7$ is a C$_1$-C$_4$ alkylene group. which is capable of delivering aldehyde-type or ketone-type fragrance compounds, providing a long-lasting release of said fragrance compounds. This compound can be incorporated into fiber conditioning compositions, such as hair conditioners and fabric softeners, to enhance the fragrance performance. The compound provides controlled release from the substrate where it has been deposited over an extended period of time.

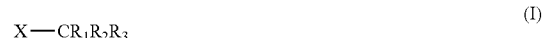

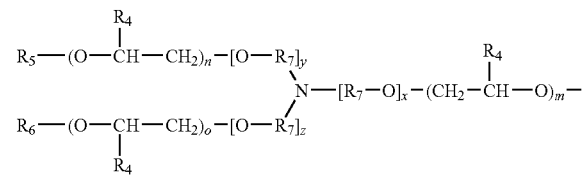

14 Claims, 1 Drawing Sheet

Figure 1

FRAGRANCE PRECURSOR

TECHNICAL FIELD

This invention relates to a compound which is capable of delivering aldehyde-type or ketone-type fragrance compounds, providing a long-lasting fragrance release, and to compositions containing said compound. The mentioned compound can be incorporated in fiber conditioning compositions, such as hair conditioners and fabric softeners.

PRIOR ART

Fragrances (any substance, natural or synthetic, used to impart an odour to a product) are frequently incorporated in detergents and other cleaning products to give a pleasant odour during use of the cleaning product and to mask the inherent smell of the soap or other surfactant present in the cleaning product.

Upon storage in a cleaning composition, fragrances can be altered through interactions and/or reactions with the other components of the composition.

Due to their volatile nature, the fragrant compounds tend to be dissipated with time, particularly the most volatile compounds which are often associated with perceived freshness.

Moreover, when used, such as during washing of fabrics with a laundry detergent, most of the perfume is also lost in the aqueous phase during the washing cycle and/or the rinsing cycle. It has been recognised as desirable that the fragrance should survive storage in the cleaning composition and also survive the cleaning process and should be deposited on the fabric, so that fabrics laundered with a detergent containing the fragrance or softened with a fabric softener containing the fragrance should have the pleasant odour of the fragrance.

Furthermore, once adsorbed onto the targeted surface, for example fabrics or hair or skin, the fragrance tends to be dissipated very quickly. A long-lasting odour, slowly emitted from the substrate (surface, fabric, skin, hair, etc.) is a desired property of the fragrances incorporated in the detergent or cleaning compositions, which is often described as substantivity, tenacity or longevity.

To incorporate fragrances in aqueous solutions containing other ingredients and to prolong their diffusion, different techniques have been applied, such as micro-encapsulation, water-in-oil or oil-in-water emulsions, cross-linked silicone gels, silicone vesicles, etc. However, in some cases these techniques cannot be used and/or do not provide appropriate results.

Another way of enhancing the substantivity of fragrances is using fragrance precursors, also known as pro-fragrances. A fragrance precursor is a compound, which may or may not be odoriferous in it-self but which upon hydrolysis produces a desirable odour, which is characteristic of one or more of its hydrolysis products. A mixture of fragrance precursor compounds can also be considered a fragrance precursor.

Different fragrance precursors are known in the prior art. Fragrance precursors of ester type are used to incorporate fragrance raw material alcohols and esters. Fragrance raw material aldehydes and ketones are incorporated via acetals, hemiacetals, ketals and hemiketals.

WO-A-2004047788 describe a class of fragrance precursor compounds comprising one or more of the compounds derived from the reaction of X—OH and an aldehyde or ketone, said fragrance precursor compounds being of the formula X—O—C(R) (R*) (OR**) wherein R is a $C_6$-$C_{24}$ alkyl group, a $C_6$-$C_{24}$ aralkyl group or a $C_6$-$C_{24}$ alkaryl group; R* is H or a $C_6$-$C_{24}$ alkyl group, a $C_6$-$C_{24}$ aralkyl group or a $C_6$-$C_{24}$ alkaryl group; R** is H or X; X—O representing a moiety derived from X—OH, and wherein X—OH is a compound selected from the group consisting of surfactants, fabric softeners, softener precursor ester amines, softener precursor amido amines, hair conditioners, skin conditions, saccharides and polymers.

According to WO-A-2004047788, the preferred fragrance precursors are the reaction product between fatty or di-amido amines with $C_8$-$C_{12}$ aldehydes. Said reaction products between fatty or di-amido amines with $C_8$-$C_{12}$ aldehydes are the only examples of fragrance precursors specifically described in WO-A-2004047788. Although said reaction products between fatty or di-amido amines with $C_8$-$C_{12}$ aldehydes have some long-lasting properties, the fragrance intensity and long-lasting effect is not completely satisfactory.

It can be concluded from the existing prior art that the industry still requires improvements in the field of the controlled release of fragrances so as in the field of the sustained release from the substrate where the fragrance has been deposited.

SUMMARY OF THE INVENTION

The present invention offers an efficient solution to the problems encountered in the prior art, by providing a compound which is capable of delivering aldehyde-type or ketone-type fragrance compounds, providing a long-lasting release of said fragrance compounds.

It has now been found that a compound of the following formula I $$X-CR_1R_2R_3 \qquad (I)$$

wherein
$R_1$ is an organic moiety having 6 to 24 carbon atoms;
$R_2$ is H or an organic moiety having 6 to 24 carbon atoms;
$R_3$ is X or OH;
X is a moiety of the following formula II:

$$\begin{array}{c} R_5-(O-\underset{R_4}{\overset{}{C}}H-CH_2)_n-[O-R_7]_y \\ \phantom{xxxxxxxxxxxxxxxxxx} \diagdown \\ \phantom{xxxxxxxxxxxxxxxxxxxxx} N-[R_7-O]_x-(CH_2-\underset{}{\overset{R_4}{C}}H-O)_m- \\ \phantom{xxxxxxxxxxxxxxxxxx} \diagup \\ R_6-(O-\underset{R_4}{\overset{}{C}}H-CH_2)_o-[O-R_7]_z \end{array} \qquad (II)$$

or an ammonium or $C_1$-$C_4$ alkyl ammonium salt of the moiety of formula II;
wherein
x is 0 or 1;
y is 0 or 1;
z is 0 or 1;
m is a number from 2 to 10;
n is a number from 0 to 10;
o is a number from 0 to 10;
$R_4$ is H or a $C_1$-$C_4$ alkyl group;
$R_5$ is a $C_6$-$C_{22}$ alkyl or alkenyl group or, if n or o is at least 1, a $C_7$-$C_{23}$ acyl group;
$R_6$ is H or $R_5$;
$R_7$ is a $C_1$-$C_4$ alkylene group,
provides an improved fragrance intensity and a long-lasting release (substantivity) of aldehyde-type or ketone-type fragrance compounds from the substrate where it has been deposited (surface, fabric, skin, hair, etc.).

The subject matter of the present invention also provides a composition comprising a mixture of at least two compounds of formula I in an aqueous solution.

The subject matter of the present invention also includes the fiber conditioning compositions, such as hair conditioners (hair-conditioning compositions) and fabric softeners (rinse conditioner compositions for fabric softening), which comprise the mentioned compound of formula I.

The subject matter of the present invention also includes the use of the compound of formula I for delaying the release of an aldehyde-type or a ketone-type fragrance compound from fibers.

The present invention also provides the use of the compound of formula I for enhancing the fragrance longevity of fiber conditioning compositions, such as hair conditioners (hair-conditioning compositions) and fabric softeners (rinse conditioner compositions for fabric softening).

The subject matter of the present invention also includes the use of the compound of formula I for enhancing the deposition of perfume on fibers.

The fiber conditioning compositions containing the compound according to the invention exhibit a significantly improvement of the fragrance intensity in said compositions when compared with compositions containing known fragrance precursors. Furthermore, the long-lasting properties of the fragrance are also significantly improved.

DETAILED DESCRIPTION OF THE INVENTION

Figure 1:
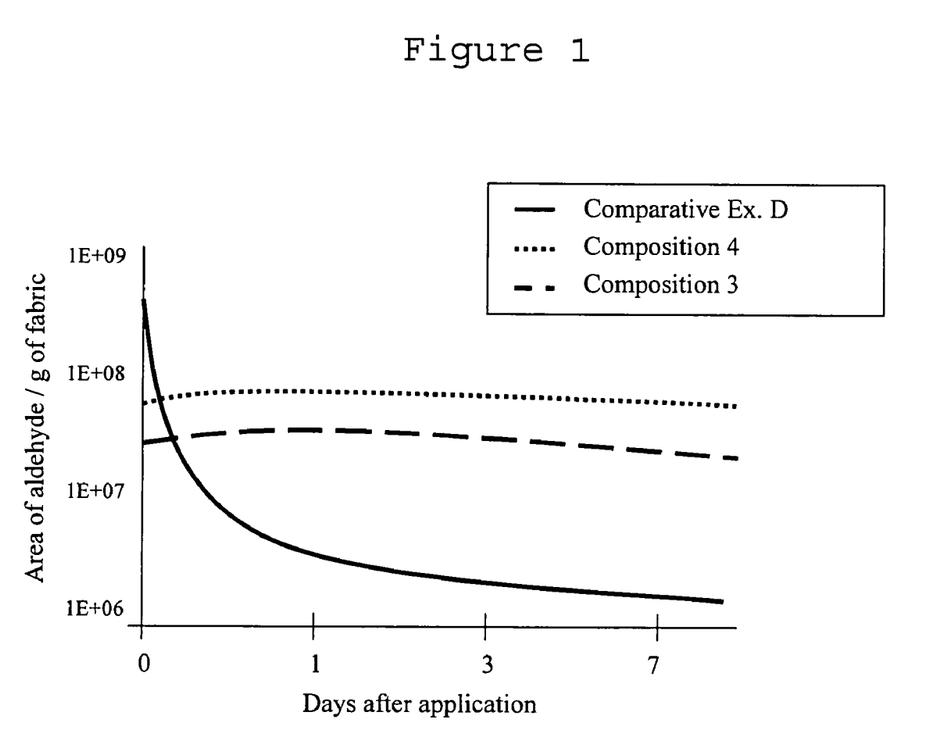
FIG. 1 shows the release of aldehyde-type fragrance compound (undec-10-enal) from towels treated with compositions 3 and 4 and also with comparative experiment D. Said release was analysed by SPME (Solid Phase Micro-Extraction) GC/MS (Gas Cromatography/Mass Spectrometry) after 0 (wet conditions) 1, 3 and 7 days.

The compound of formula I is preferably obtainable by reacting X—H, wherein X has the same meaning as previously indicated, with a compound of the formula $R_1COR_2$, wherein $R_1$ and $R_2$ have the same meaning as previously indicated.

Therefore, hemiacetal, acetal, hemiketal or ketal compounds are obtained. Ketals and acetals are preferred, particularly preferred being acetals.

The formation of a hemiacetal, an acetal or mixtures thereof, involves the reaction of a compound comprising at least one free —OH group with an aldehyde. Additionally, the formation of a hemiketal, a ketal or mixtures thereof, involves the reaction of a compound comprising at least one free —OH group with a ketone.

These reactions are known per se. Preferably, these reactions are carried out in an aqueous solution in the presence of an acid or a catalyst, for example hydrochloric acid, paratoluene sulphonic acid or supported sulfonic acid, at temperatures between 25° C. and 90° C., preferably between 35° C. and 85° C., even more preferably between 40° C. and 80° C.

The molar ratio of the aldehyde or ketone to X—H is generally in the range from 1.0:1.0 to 3.0:1.0, more preferably from 1.2:1.0 to 2.8:1.0.

The Aldehydes and Ketones

The aldehydes or ketones used for the production of the compounds of the present invention are fragrances, i.e. compounds having a characteristic, usually pleasant odor. Fragrances are generally volatile. Hence, the said compound of the formula $R_1COR_2$ has preferably a molecular weight (molecular mass) of less than 300 g/mol, more preferably 200 g/mol.

In the formula $R_1COR_2$ $R_1$ is an organic moiety having 6 to 24 carbon atoms; and $R_2$ is H or an organic moiety having 6 to 24 carbon atoms. The organic moiety in $R_1$ or $R_2$ is generally a saturated or unsaturated hydrocarbon group which may have one or more substituents, such as OH, halogen (such as F, Cl, Br), COOH etc. The hydrocarbon group may also have an ether (—O—), thioether (—S—), or carbonyl (—C=O) (including esters or aldehydes) functionality. Most preferred are hydrocarbon groups having 6 to 24 carbon atoms, particularly 6 to 16 carbon atoms, without any functional groups.

According to the invention, it is particularly preferred that the compound of the formula R1COR2 is an aliphatic aldehyde or ketone, a cycloaliphatic aldehyde or ketone, an acyclic terpene aldehyde or ketone, a cyclic terpene aldehyde or ketone, an aromatic aldehyde or ketone, or a phenol aldehyde or ketone.

The aldehydes useful in the present invention can be one or more of, but not limited to, the following group of aldehydes: phenylacetaldehyde, p-methyl phenylacetaldehyde, p-isopropyl phenylacetaldehyde, methylnonyl acetaldehyde, phenylpropanal, 3-(4-t-butylphenyl)-2-methyl propanal, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methylpropanal, 3-(4-ethylphenyl)-2,2-dimethylpropanal, phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal (melonal), 2,6-dimethylpropanal, 2,4-heptadienal, octanal, 2-octenal, 3,7-dimethyloctanal, 3,7-dimethyl-2,6-octadien-1-al, 3,7-dimethyl-1,6-octadien-3-al, 3,7-dimethyl-6-octenal, 3,7-dimethyl-7-hydroxyoctan-1-al, nonanal, 6-nonenal, 2,4-nonadienal, 2,6-nonadienal, decanal, 2-methyl decanal, 4-decenal, 9-decenal, 2,4-decadienal, undecanal, 2-methyldecanal, 2-methylundecanal, 2,6,10-trimethyl-9-undecenal, undec-10-enyl aldehyde, undec-8-enanal, dodecanal, tridecanal, tetradecanal, anisaldehyde, bourgenonal, cinnamic aldehyde, α-amylcinnam-aldehyde, α-hexyl cinnamaldehyde, methoxy cinnamaldehyde, citronellal, hydroxy-citronellal, isocyclocitral, citronellyl oxyacet-aldehyde, cortexaldehyde, cumminic aldehyde, cyclamem aldehyde, florhydral, heliotropin, hydrotropic aldehyde, lilial, vanillin, ethyl vanillin, benzaldehyde, p-methyl benzaldehyde, 3,4-dimethoxybenzaldehyde, 3- and 4-(4-hydroxy-4-methyl-pentyl)-3-cyclohexene-1-caroxaldehyde, 2,4-dimethyl-3-cyclohexene-1-carboxaldehyde, 1-methyl-3-4-methylpentyl-3-cyclohexencarboxaldehyde, and p-methylphenoxyacetaldehyde.

According to the invention, aldehydes not α-substituted are preferred, i.e. aldehydes having no substituent group at the carbon atom adjacent to the carbonyl group.

The ketones useful in the present invention can be one or more of, but not limited to, the group of following ketones: α-damascone, β-damascone, δ-damascone, β-damascenone, muscone, 6,7-dihydro-1,1,2,3,3-pentamethyl-4(5H)-indanone, cashmeran, cis-jasmone, dihydrojasmone, methyl dihydrojasmonate, α-ionone, β-ionone, dihydro-β-ionone, γ-methyl ionone, α-iso-methyl ionone, 4-(3,4-methylenedioxyphenyl)butan-2-one, 4-(4-hydroxyphenyl)butan-2-one, methyl β-naphthyl ketone, methyl cedryl ketone, 6-acetyl-1,1,2,4,4,7-hexamethyltetralin (tonalid), 1-carvone, 5-cyclohexadecen-1-one, acetophenone, decatone, 2-[2-(4-methyl-3-cyclohexenyl-1-yl)propyl]cyclopentan-2-one, 2-sec-butylcyclohexanone, β-dihydro ionone, allyl ionone, α-irone, α-cetone, α-irisone, acetanisole, geranyl acetone, 1-(2-methil-5-isopropyl-2-cyclohexenyl)-1-propanone, acetyl diisoamylene, methyl cyclocitrone, 4-t-pentyl cyclohexanone, p-t-butylciclohexanone, o-t-butylcyclohexanone, ethyl amyl ketone, ethyl pentyl ketone, menthone, methyl-7,3-dihydro-2H-1,5-benzodioxepine-3-one, fenchone, methyl naphthyl ketone, propyl naphthyl ketone and methyl hydroxynaphthyl ketone.

According to the invention, ketones not α-substituted are preferred, i.e. ketones having no substituent group at the carbon atom adjacent to the carbonyl group.

The Moiety of Formula II

Preferred values for m in formula II are in the range of 3 to 8. It is also preferred that the sum of m, n, and o is in the range of 10 to 20.

Preferably, in formula II $R_4$ is H and $R_6$ is $R_5$.

Particularly preferred moieties of formula II are those wherein x, y, and z are each 1, $R_7$ is an ethylene group, and $R_5$ is a $C_9$-$C_{19}$ acyl group.

Other preferred moieties of formula II are those wherein x, y, z, and n are each 0, and $R_5$ is a $C_6$-$C_{22}$ alkyl or alkenyl group. More preferably, wherein o is 0, and $R_6$ is $R_5$.

Other preferred moieties of formula II are those wherein x, y, z, and n are each 0, and $R_5$ is a $C_6$-$C_{22}$ alkyl or alkenyl group, and o is a number from 2 to 10, and $R_6$ is H.

Preferably, the moiety of formula II is derived from an amine derivative selected from alkoxylated esteramines and alkoxylated fatty amines, or mixtures thereof, or their corresponding ammonium or $C_1$-$C_4$ alkyl ammonium salts, or mixtures thereof.

Particularly preferred moieties of formula II are derived from alkoxylated esteramines of formula (1), $$R_4-N \begin{cases} R_2-O-(CH_2-\underset{R_3}{CH}-O)_m-\overset{O}{\underset{\|}{C}}-R \\ R_2-O-(CH_2-\underset{R_3}{CH}-O)_n-R_1 \end{cases} \quad (1)$$

wherein
n is a number from 2-10, more preferably from 3 to 8
m is a number from 0 to 10, more preferably from 3 to 8,
R is a linear or branched, saturated or unsaturated $C_6$-$C_{22}$ alkyl or alkenyl group, preferably a linear or branched, saturated or unsaturated $C_8$-$C_{18}$ alkyl or alkenyl group,
$R_1$ is hydrogen or a —CO—R group,
$R_2$ is a $C_1$-$C_4$ alkylene group, preferably a ethylene group
$R_3$ is hydrogen or a $C_1$-$C_4$ alkyl group, preferably hydrogen or methyl, even more preferably hydrogen
$R_4$ is hydrogen, a $C_1$-$C_4$ alkyl group or a group $$-R_2-O-(CH_2-\underset{R_3}{CH}-O)_p-R_1$$

wherein $R_1$, $R_2$ and $R_3$ have the same meaning as above, and p is a number from 0 to 10, preferably from 3 to 8,
wherein at least one R1 represents hydrogen,
or their corresponding ammonium or $C_1$-$C_4$ alkyl ammonium salts, or mixtures thereof.

Other preferred moieties of formula II are derived from alkoxylated fatty amines of formula (2), $$R_5-N \begin{cases} (CH_2-CH-O)_a-H \\ | \\ R_7 \\ R_6 \end{cases} \quad (2)$$

wherein
a is a number from 2 to 10, preferably from 3 to 8,
$R_7$ is hydrogen or a $C_1$-$C_4$ alkyl group, preferably hydrogen or methyl, more preferably hydrogen
$R_5$ and $R_6$ are each independently
methyl,
a linear or branched, saturated or unsaturated $C_8$-$C_{22}$ alkyl or alkenyl group, preferably a linear or branched, saturated or unsaturated $C_8$-$C_{18}$ alkyl or alkenyl group, or
a —(CH$_2$—CHR$_7$—O)$_b$—H group, wherein b is a number from 0 to 10, preferably from 3 to 8, and $R_7$ has the same meaning as above,
or their corresponding ammonium or $C_1$-$C_4$ alkyl ammonium salts, or mixtures thereof.

The Alkoxylated Esteramines

The alkoxylated esteramines of formula (1) can be obtained by the condensation of a $C_6$-$C_{22}$ fatty acid with an alkoxylated alkanolamine. Alternative, the alkoxylated esteramines of formula (1) can also be obtained by the alkoxylation of the condensation product of a $C_6$-$C_{22}$ fatty acid with an alkanolamine.

Examples of suitable $C_6$-$C_{22}$ fatty acids are those obtained from vegetable and animal oils and fats such those obtained from castor oil, coconut oil, corn oil, mustard oil, olive oil, palm oil, peanut oil, rapeseed oil, sunflower oil, soybean oil, tall oil, tallow, eventually totally or partially hydrogenated, as well as purified or synthetic fatty acids, like caproic acid, caprylic acid, capric acid, isotridecanoic acid, lauric acid, myristic acid, palmitic acid, palmoleic acid, stearic acid, isostearic acid, 2-ethylhexanoic acid, oleic acid, elaidinic acid, petroselenic acid, linoleic acid, linolenic acid, eleostearic acid, ricinoleic acid, arachidic acid, gadoleic acid, behenic acid, erucic acid, or their technical-grade mixtures.

The fatty acid is preferably a $C_8$-$C_{18}$ acid containing a degree of unsaturation such that the iodine value ("IV") is in the range from 0-90, preferably from 10-90, more preferably in the range from 15-85.

It is also preferred that the fatty acid(s) employed in the present process have a cis to trans isomer ratio from 80:20 to 95:5. More preferably, the trans isomer content of said fatty acid(s) is less than 10%. An optimum trans-isomer content is between 0.5-5%.

Suitable alkanolamines are triethanolamine, N-methyldiethanolamine, N-methyldiisopropanolamine, propanoldiethanolamine, ethanoldiisopropanolamine and triisopropanolamine, or mixtures thereof, preferably triethanolamine and N-methyldiethanolamine, even more preferably triethanolamine.

As explained before, the alkoxylated esteramines of formula (1) can be obtained either by the condensation of a $C_6$-$C_{22}$ fatty acid with an alkoxylated alkanolamine, or by the alkoxylation of the condensation product of a $C_6$-$C_{22}$ fatty acid with an alkanolamine. In both cases, the alkoxylation degree is preferably from 1 to 10, more preferably from 3 to 8 units of ethylene oxide, propylene oxide or butylene oxide per hydroxyl group of the alkanolamine. According to the invention, it is preferred that ethylene oxide is the alkoxylation agent.

The esterification of fatty acids with alkanolamines (alkoxylated or not) can be carried out by known methods, such as it is described in ES-A-2021900.

It is preferred that the esterification of fatty acids with (alkoxylated) alkanolamines or mixtures thereof is carried out at a temperature of between 120° C. and 220° C., for a period of from 2 to 10 hours, preferably at a reduced pressure of 5 to 200 mbar and in the presence of some of the catalysts already known for the esterification, for example, hypophosphorous acid and paratoluene sulphonic acid, and also in the presence of some of the usual stabilizers and antioxidants such as tocopherols, BHT, BHA, citric acid, etc.

The molar ratio of fatty acid to (alkoxylated) alkanolamine is generally in the range from 1.0:1.0 to 3.0:1.0

The reaction product of the esterification reaction is a complex mixture of mono-, di- and triesters of fatty acids or mono- and di-esters, depending of the number of hydroxyl groups of the (alkoxylated) alkanolamine that have been reacted with the fatty acid.

When the (alkoxylated) alkanolamine derives from the triethanolamine, it is preferred that the reaction product is a mixture comprising from 19 to 35% by weight, preferably from 40 to 60% by weight, of the monoester, from 40 to 60% by weight, preferably from 46 to 52% by weight, of the diester, and from 10 to 40% by weight, preferably from 16 to 35% by weight, of the triester.

The ammonium salts of the alkoxylated esteramines of formula (1) can be obtained by neutralization with organic or inorganic acids.

The $C_1$-$C_4$ alkyl ammonium salts alkoxylated esteramines of formula (1) can be obtained using alkylating agents (methyl chloride, dimethyl sulfate, etc.) and methods well-known by the skilled in the art.

The Alkoxylated Fatty Amines

The alkoxylated fatty amines of formula (2) are obtained by alkoxylation of primary or secondary fatty amines under standard conditions known by the skilled in the art. For instance, the polyoxyalkylene group is obtained by addition of ethylene oxide, propylene oxide or butylene oxide to primary or secondary fatty amines, mostly with an alkaline catalyst such as NaOH, KOH or $NaOCH_3$, giving a broad polyoxyalkylene distribution (broad alkoxylation degree). For special applications the alkoxylation can be catalyzed by Lewis acids or by using metallic Na, NaH or hydrotalcite catalysts to achieve a narrow range distribution (narrow alkoxylation degree). Preferably, the alkoxylated fatty amines of formula (2) are alkoxylated with 1 to 10, preferably with 3 to 8 units of ethylene oxide, propylene oxide or butylene oxide, being preferred the fatty amines alkoxylated with ethylene oxide.

The alkoxylated fatty amines of formula (2) are derived from fatty acids. Examples of suitable fatty acids are those obtained from vegetable and animal oils and fats such those obtained from castor oil, coconut oil, corn oil, mustard oil, olive oil, palm oil, peanut oil, rapeseed oil, sunflower oil, soybean oil, tall oil, tallow, eventually totally or partially hydrogenated, as well as purified or synthetic fatty acids, like caproic acid, caprylic acid, capric acid, isotridecanoic acid, lauric acid, myristic acid, palmitic acid, palmoleic acid, stearic acid, isostearic acid, 2-ethylhexanoic acid, oleic acid, elaidinic acid, petroselenic acid, linoleic acid, linolenic acid, eleostearic acid, ririnoleic acid, arachidic acid, gadoleic acid, behenic acid, erucic acid, or their technical-grade mixtures.

The alkoxylated fatty amines of formula (2) are preferably alkoxylated primary or secondary $C_8$-$C_{18}$ fatty amines or mixture thereof, even more preferably alkoxylated secondary fatty amines having two linear or branched, saturated or unsaturated $C_8$-$C_{18}$ alkyl or alkenyl groups.

The alkoxylated fatty amines of formula (2) preferably contain a degree of unsaturation such that the iodine value ("IV") is in the range from 0-90, preferably from 10-70, more preferably in the range from 0-18.

It is also preferred that the alkoxylated fatty amines of formula (2) employed in the present invention have a cis to trans isomer ratio from 80:20 to 95:5. More preferably, the trans isomer content of said alkoxylated fatty amines is less than 10%. An optimum trans-isomer content is between 0.5-5%.

Examples of suitable alkoxylated fatty amines of formula (2) are AMIET® DT/17 (secondary tallow amine with an average ethoxylation degree of 5), AMIET® DC/24 (secondary coconut amine with an average ethoxylation degree of 12), AMIET® DO/17 (secondary oleyl amine with an average ethoxylation degree of 5), all produced by KAO Chemicals Europe.

Examples of commercially available amines that can be alkoxylated are FARMIN® 20D (distilled dodecylamine), FARMIN® 80D (distilled octadecylamine), FARMIN® CD (primary coco amine), FARMIN® OD (primary oleyl amine), FARMIN® T (primary tallow alkyl amine), FARMIN® DTH (secondary di(hydrogenated tallow) amine), all marketed by KAO Chemicals Europe.

The ammonium salts of the alkoxylated fatty amines of formula (2) can be obtained by neutralization with organic or inorganic acids.

The $C_1$-$C_4$ alkyl ammonium salts of the alkoxylated fatty amines of formula (2) can be obtained using alkylating agents (methyl chloride, dimethyl sulfate, etc.) and methods well-known by the skilled in the art.

The Compound of Formula I

The compound of formula I of the present invention provides a delay of the release of an aldehyde-type or ketone-type fragrance compound and a long-lasting aldehyde-type or ketone-type fragrance compound release (substantivity) from the substrate where said compound of formula I has been deposited, like hard-surface, fabric (textile), skin, hair, etc.

Said substrate are preferably fibers, which can be natural or synthetic fibers. According to the present invention, synthetic fibers are fibers of chemical origin, which are defined as fibers obtained by physical or chemical processes in production means, which comprises cellulosic and synthetic fibers as described in the "Kirk-Othmer Encyclopedia of Chemical Technology", third edition, volume 10, published by Wiley-Interscience (ISBN 0-471-02095-3). Examples of fibers of chemical origin are     acrylic, polyamide, polyester and polyurethane; while fibers of synthetic origin are,     acetate and rayon, which are of cellulosic origin.

Examples of fibers of natural origin are:

cotton, from vegetable origin;

camel, cashmere, silk and wool, which are of animal origin; and     human hair.

The use of a compound of formula I according to the invention for delaying the release of an aldehyde-type or ketone-type fragrance compound from fibers is also included in the subject of the present invention.

The use of the compound of formula I for enhancing the deposition of perfume on fibers is also included in the subject of the present invention.

The fragrance compound (aldehyde or ketone) derivable from the compound of formula I of the present invention is only released when said compound of formula I is broken down.

A composition comprising a mixture of at least two compounds of formula I in an aqueous solution is also included in the subject of the present invention.

The compound of formula I according to the invention can be used as the sole fragrance compound in compositions for the conditioning of fibers, or in combination with other fragrance precursors and/or in combination with other fragrance compounds, extenders, fixatives, diluents and the like.

The Hair Conditioners

The use of a compound of formula I according to the invention for enhancing the fragrance longevity of a hair conditioner (hair-conditioning composition) is also included in the subject of the present invention.

The use of a compound of formula I of the present invention in hair conditioners is particularly preferable in view of the improvement of the fragrance performance and the long lasting properties.

The present invention also provides hair conditioners comprising at least one compound of formula I according to the invention in which the fragrance precursor is present in quantities from 0.0001% to 10%, more preferably from 0.001% to 5%, even more preferably, from 0.01% to 1.5% by weight with respect to the total weight of the hair conditioners.

The present invention also provides hair conditioners comprising at least one compound of formula I according to the invention and a hair conditioning compound of formula X—H, or the corresponding ammonium or $C_1$-$C_4$ alkyl ammonium salt thereof, wherein X has been previously defined.

Hair conditioners are usually aqueous liquids containing a range of materials designed to improve the shine, body and manageability of the hair, the hair conditioning agents being present at 2-60%, typically 2-10% (as active matter) expressed as weight percentage based on the total composition. The conditioning materials consist of non-ionic, amphoteric or cationic polymers (for example hydroxyethyl cellulose, polyquarternium-39, guar hydroxypropyl-trimonium chloride, polyquarternium-10 and quaternised keratin), non-ionic, cationic and amphoteric surfactants (for example stearyl dimethyl benzyl ammonium chloride, ethoxylated fatty alcohols, ethoxylated esters of fatty alcohols and cetyl trimethyl ammonium bromide) and oils and waxes (for example cetearyl alcohol, silicone oils, mineral oils, natural oils such as avocado and jojoba oils, and glycerol esters). Suitable hair conditioners may also contain other ingredients, including solvents, vitamins, hair nourishing ingredients, dyes, preservatives and pH control agents. Hair conditioners can be designed either to be left on the hair after use or to be rinsed out.

The total amount of the surfactant base (surfactant or mixture of surfactants) is in the range of 1 to 25% by weight, preferably from 5 to 20% by weight with respect to the total weight of the hair conditioner composition.

Typical examples of cationic surfactants are quaternary ammonium salts (quats) and the quaternized derivatives of polyalkanolamine esters (esterquats). Examples of commercially available quats are: QUARTAMIN® AB (Behentrimonium Chloride), QUARTAMIN® 60W25 (Cetrimonium Chloride) and QUARTAMIN® ABK (Behentrimonium Chloride and Cetearyl Alcohol), all marketed by KAO Chemicals Europe.

Examples of commercially available esterquats are QUARTAMIN® BTC-131 (Behenoyl PG-Trimonium Chloride), marketed by KAO Chemicals Europe, and TETRANYL® CO-40 (Dioleoylethyl Hydroxyethylmonium Methosulfate and Dipropylene Glycol) marketed by KAO Chemicals Europe.

Specific examples of non-ionic surfactants are mixtures of alkoxylated glycerides and alkoxylated glycerine, like the commercially available under the trademark LEVENOL® marketed by KAO Chemicals Europe, alkoxylated trimethyolol propane, alkoxylated 1,2,3-trihydroxy hexane, alkoxylated pentaetrythritol, alkoxylated sorbitol, alkoxylated glycerol, alkoxylated glycerol fatty acid ester, alkoxylated trimethyolol propane fatty acid ester, alkoxylated 1,2,3-trihydroxy hexane fatty acid ester, alkoxylated pentaetrythritol fatty acid ester, alkoxylated sorbitol fatty acid ester, fatty alcohol polyglycol ethers, alkylphenol polyglycol ethers, fatty acid polyglycol esters, $C_6$-$C_{22}$ fatty alcohols, fatty acid amide polyglycol ethers, fatty amine polyglycol ethers, mixed ethers and mixed formals, optionally partly oxidized alk(en)yl oligoglycosides or glucuronic acid derivatives, fatty acid-N-alkylglucamides, protein hydrolyzates (particularly wheat-based vegetable products), polyol fatty acid esters, sugar esters, alkyl polyglucosides, sorbitan esters, polysorbates and alkanolamides, including alkoxylated alkanolamides and alkyl ether carboxylic acid alkanolamides.

Amphoteric surfactant includes ampholytes and betaines. Specific examples are alkyl amine oxides, alkyl betaines, alkyl sulphobetaines (sultaines), amidoalkyl betaines, alkyl glycinates, alkyl carboxyglycinates, alkyl amphoacetates, alkyl amphopropionates, alkylamphoglycinates, alkyl amidopropyl betaines, alkyl amidopropyl- and hydroxysultaines. Particularly preferred amphoteric surfactants are alkyl amine oxides, alkyl sulphobetaines (sultaines), alkylamphoglycinates alkyl amphoacetates such as sodium coco monoamphoacetate or sodium coco diamphoacetate, and alkyl amidopropyl betaines such as cocoamido propyl betaine.

The hair conditioners according to the present invention can also comprise, as further auxiliaries and additives, superfatting agents, pearlescent waxes, bodying agents, thickeners, polymers, silicone compounds, fats, waxes, stabilizers, biogenic active ingredients, deodorants, antiperspirants, anti-dandruff agents, film formers, UV light protection factors, antioxidants, preservatives, insect repellents, self-tanning agents, tyrosine inhibitors (depigmentation agents), solubilizers, perfume oils, dyes and the like.

The hair conditioners according to the present invention have a range of viscosities from 10 to 100,000 centipoise (cP) at $10\ s^{-1}$ shear rate, in the case of leave-on products and a range of viscosities from 10,000 to 100,000 centipoise (cP) at $10\ s^{-1}$ shear rate in the case of rinse-off products.

The Fabric Softeners

The use of a compound of formula I according to the invention for enhancing the fragrance longevity of a fabric softener (rinse conditioner composition for fabric softening) is also included in the subject of the present invention.

The use of a compound of formula I of the present invention in fabric softeners (rinse conditioner compositions for fabric softening) is particularly preferable in view of the improvement of the fragrance performance and the long lasting properties.

The use of a compound of formula I according to the invention for delaying the release of an aldehyde-type or ketone-type fragrance compound from fibers, preferably human hair, is also included in the subject of the present invention.

The use of the compound of formula I for enhancing the deposition of perfume on fibers, preferably human hair, is also included in the subject of the present invention.

The present invention also fabric softeners comprising at least one compound of formula I according to the invention in which the compound of formula I is present in quantities from 0.0001% to 10%, more preferably from 0.001% to 5%, even more preferably, from 0.01% to 1.5% by weight with respect to the total weight of the fabric softeners.

The present invention also provides fabric softeners comprising at least one compound of formula I according to the invention and a fabric softening compound of formula X—H, or the corresponding ammonium or $C_1$-$C_4$ alkyl ammonium salt thereof, wherein X has been previously defined.

A fabric (textile) softener contains at least one softening agent, which functions to give the fabric a softer handle. Frequently such agents also provide an anti-static benefit. Such agents are usually cationic, but may be nonionic, amphoteric or zwitterionic materials.

Cationic surfactants that act as textile-softeners and that may constitute one of the components of the fabric softener compositions according the invention are well known by the skilled person.

Specific examples of fabric softening agents are acrylic quaternary ammonium compounds, diamido quaternary ammonium salts, ester quaternary ammonium salts (esterquats), quaternary imidazolinium salts and the like.

Among these, mention may be made of quaternary ammonium compounds whose hydrophobic chains are not interrupted by an ester group, for example those described in patents U.S. Pat. No. 4,719,382 and U.S. Pat. No. 4,237,016, of which the most well known is hydrogenated tallow dialkyldimethylammonium chloride, also known as DTDMAC, such as that marketed by KAO Chemicals Europe under the trademark QUARTAMIN® D86P.

However, according to the invention, the following esterquats, are preferred:
 the quaternised diesters of fatty acids with 1,2-dihydroxy-3-dimethylaminopropane, such as described by U.S. Pat. No. 4,137,180 and European patent application EP-A-0585040,
 the quaternised diesters of fatty acids with N-methyldiethanolamine, such as those described in French patent application FR-A-1593921 and in European patent EP-B-0239910, for example the hydrogenated tallow diester quaternised with methyl chloride and marketed by KAO Chemicals Europe under the trademark KAOSOFT® PH,
 the amido ester salts of fatty acids with N-methyl-N-aminopropylethanolamine, for example that marketed by KAO Corporation Japan under the trademark KAOSOFT® 1,
 the quaternised diesters of fatty acids with triethanolamine, such as those described in U.S. Pat. No. 3,915,867 and in a large number of later patents, for example the diesters of partially hydrogenated tallow which are quaternised with dimethyl sulphate and which are marketed by KAO Chemicals Europe under the trademark TETRANYL® AT-7590, TETRANYL® L1/90S, and other quaternised diesters such as TETRANYL® AT-1 and TETRANYL® AT1/DP (Tallow base) and TETRANYL® AO-1 and TETRANYL® AOT-1 (Oleyl base)

It should be pointed out that when reference is made to the term "diester" this is intended to indicate that the diester predominates in the mixture, although the product may always contain variable amounts of monoester compounds and, in the case of triethanolamine, triester compounds.

There also come into consideration as cationic surfactants having a softening character, the oligomeric cationic surfactants,
 esterquats derived from dicarboxylic acids, fatty acids and alkanolamines as described in the international patent application WO-A-9849132, for example those marketed by KAO Chemicals Europe under the references TETRANYL® PH-2 and TETRANYL® PH-5,
 or esterquats obtained from alkanolamine esters based on the esterification reaction of optionally alkoxylated alkanolamines with dicarboxylic acids, fatty acids and fatty alcohols which are optionally alkoxylated, as described in the European patent application EP-A-1136471, for example those marketed by KAO Chemicals Europe under the references TETRANYL® CL-518.

The non-ionic surfactants that condition textiles or other fibers and that may be also present in the fabric softener according to the invention, are also well known to the person skilled in the art and of these there may be mentioned: fatty acids and their esters, especially those containing from 8 to 18 carbon atoms, which are linear or branched and alkoxylated or non-alkoxylated; alkoxylated or non-alkoxylated Guerbet alcohols; esters of glycerol and polyglycerol, for example HOSTACERIN DGMS and HOSTACERIN DGI marketed by Clariant; xylitol esters; alkoxylated or non-alkoxylated sorbitan esters, for example KAOPAN marketed by KAO Chemicals Europe; esters of sugars, such as glucose, fructose, galactose, mannose, xylose, arabinose ribose, 2-deoxyribose and sucrose; $C_6$-$C_{22}$ fatty alcohols; mixtures of alkoxylated glycerides and alkoxylated glycerine, which are commercially available under the trademark LEVENOL® marketed by KAO Chemicals Europe; ethoxylated polyglycerol esters, for example HOSTACERIN DGL and HOSTACERIN DGSB marketed by Clariant; alkyl polyglucosides, for example AG-10LK, marketed by KAO Corporation Japan; and alkoxylated or non-alkoxylated pentaerythritol esters, for example RADIA 7171 and RADIA 7176, marketed by Oleofina. Also exhibiting a good conditioning power are non-ionic surfactants with amide groups, among which there may be mentioned derivatives of amine, such as glucamine, for example MEDIALAN GAC and MEDIALAN GAL marketed by Clariant, and also derivatives of methylethanolamine, diethanolamine, isopropanolamine and monoethanolamine, with linear or branched fatty acids, especially C8-18 fatty acids. Finally, it can also be mentioned the esteramines described in the European patent application EP-A-443313.

Other non-ionic compounds which may be used as textile-conditioners are waxes, such as paraffins, microcrystalline waxes derived from petroleum, and synthetic waxes.

Of all the non-ionic surfactants described, the following are especially preferred: mixtures of alkoxylated glycerides and alkoxylated glycerine, sorbitan monoesters and pentaerythritol esters, especially those having a tallow, hydrogenated tallow, palm, behenic or oleic chain.

In referring to other optional components, without this having to be regarded as an exhaustive description of all possibilities, which, on the other hand, are well known to the person skilled in the art, the following may be mentioned:
 a) other products that enhance the performance of the softening compositions, such as silicones, amine oxides, anionic surfactants, such as lauryl ether sulphate or lauryl sulphate, amphoteric surfactants, such as cocoamidopropyl betaine or alkyl betaines, sulphosuccinates, polyglucoside derivatives, etc.
 b) stabilising products, such as salts of amines having a short chain, which are quaternised or non-quaternised, for example of triethanolamine, N-methyldiethanolamine, etc., and also non-ionic surfactants, such as ethoxylated fatty alcohols, ethoxylated fatty amines, ethoxylated alkyl phenols, etc.

c) products that improve viscosity control, for example inorganic salts, such as calcium chloride, magnesium chloride, calcium sulphate, sodium chloride, etc.; products which can be used to reduce viscosity in concentrated compositions, such as compounds of the glycol type, such as, for example, ethylene glycol, dipropylene glycol, polyglycols, etc.; and thickening agents for diluted compositions, for example, polymers derived from cellulose, guar gum, etc.

d) components for adjusting the pH, which is preferably from 1.5 to 4.5, such as any type of inorganic and/or organic acid, for example hydrochloric, sulphuric, phosphoric, citric acid etc.

e) agents that improve soil release, such as the known polymers or copolymers based on terephthalates.

f) bactericidal preservative agents, such as formol, Kathon GC, Bronopol, etc.

g) other products such as antioxidants, colouring agents, perfumes, germicides, fungicides, anti-corrosive agents, anti-crease agents, opacifiers, optical brighteners, pearl lustre agents, etc.

The fabric softeners can be obtained by simply mixing their components until they have been dispersed or dissolved, using methods well known by the person skilled in the art.

A fabric softener which is intended to be added during the washing cycle and/or the rinsing cycle rinse may be in the form of a solid, a powder or tablet for instance.

According to the invention, the fabric softener is preferably in the form of a liquid, and is an aqueous dispersion in water. Such a fabric softener may contain from 1% to 15% weight of a fabric softening agent in the case of standard (diluted) fabric softener but may contain higher levels from up to 30% or even 40% by weight in the case of very concentrated fabric softeners. The composition will usually also contain water and other additives, which may provide the balance of the composition.

Liquid fabric softeners are customarily prepared by melting the softening ingredients and adding the melt to hot water, with agitation to disperse the water-insoluble ingredients.

The total amount of the surfactant base (surfactant or mixture of surfactants) in the fabric softeners according to the invention is in the range of 1 to 80% by weight, preferably from 5 to 55% by weight, with respect to the total weight of the fabric softener.

The following examples are given in order to provide a person skilled in the art with a sufficiently clear and complete explanation of the present invention, but should not be considered as limiting of the essential aspects of its subject, as set out in the preceding portions of this description.

EXAMPLES

Example 1

Condensation of C10 Aldehyde with an Ethoxylated Esteramine

In a reaction flask equipped with a stirrer and a temperature probe, 50 g (0.0491 moles) of an ethoxylated esteramine derived from triethanolamine and oleic acid having on average 5.5 moles of ethylene oxide per hydroxyl group were heated at 50° C. in an oil.

Later, 0.1327 g (0.00737 moles) of water and 0.0845 g (0.00049 moles) of p-toluenesulfonic acid monohydrate were added keeping the temperature at 50° C.

Finally, 11.52 g (0.0737 moles) of decanal (decyl aldehyde) were added slowly during 1-2 hours keeping the temperature at 50° C.

Upon completion of the addition, stirring of the reaction mixture continued for further 3 hours at 50° C.

The reaction mixture was maintained overnight at 50° C. The reaction mixture was then cooled to room temperature.

Example 2

Condensation of C10 Aldehyde with an Ethoxylated Amine

In a reaction flask equipped with a stirrer and a temperature probe, 40 g (0.0671 moles) of an ethoxylated di-lauryl amine having on average 5.5 moles of ethylene oxide were heated at 60° C. in an oil bath until said ethoxylated amine was melted.

Later, 0.1813 g (0.01007 moles) of water and 0.1155 g (0.00067 moles) of p-toluenesulfonic acid monohydrate were added keeping the temperature at 60° C.

Finally, 15.74 g (0.1007 moles) of decanal (decyl aldehyde) were added slowly during 1-2 hours keeping the temperature at 60° C.

Upon completion of the addition, stirring of the reaction mixture continued for further 3 hours at 60° C. The reaction mixture was maintained overnight at 60° C. The reaction mixture was then cooled to room temperature.

Example 3

Condensation of C11 Aldehyde with an Ethoxylated Esteramine

In a reaction flask equipped with a stirrer and a temperature probe, 50 g (0.0491 moles) of an ethoxylated esteramine derived from triethanolamine and oleic acid having on average 5.5 moles of ethylene oxide per hydroxyl group were heated at 50° C. in an oil.

Later, 0.1327 g (0.00737 moles) of water and 0.0845 g (0.00049 moles) of p-toluenesulfonic acid monohydrate were added keeping the temperature at 50° C.

Finally, 12.41 g (0.0737 moles) of undec-10-enal (undec-10-enyl aldehyde) were added slowly during 1-2 hours keeping the temperature at 50° C.

Upon completion of the addition, stirring of the reaction mixture continued for further 3 hours at 50° C.

The reaction mixture was maintained overnight at 50° C. The reaction mixture was then cooled to room temperature.

Example 4

Condensation of C11 Aldehyde with an Ethoxylated Amine

In a reaction flask equipped with a stirrer and a temperature probe, 40 g (0.0671 moles) of an ethoxylated di-lauryl amine having on average 5.5 moles of ethylene oxide were heated at 60° C. in an oil bath until said ethoxylated amine was melted.

Later, 0.1813 g (0.01007 moles) of water and 0.1155 g (0.00067 moles) of p-toluenesulfonic acid monohydrate were added keeping the temperature at 60° C.

Finally, 16.95 g (0.1007 moles) of undec-10-enal (undec-10-enyl aldehyde) were added slowly during 1-2 hours keeping the temperature at 60° C.

Upon completion of the addition, stirring of the reaction mixture continued for further 3 hours at 60° C.

The reaction mixture was maintained overnight at 60° C. The reaction mixture was then cooled to room temperature.

Example 5

Fabric Softeners

Fabric softener compositions shown in Table 1 were prepared according to following procedure.

Compositions A-D are comparative examples while compositions 1-4 are according to the invention.

Esterquat (softening agent), a standard perfume and the corresponding compound as indicated in Table 1 were co-melt at 55-60° C. Water was heated to 40° C., and the co-melt was added at 40° C. to the water under stirring, at 150 rpm. Said mixture was stirred for 15 min. Then the mixture was cooled down to 25° C. at a gradient of 1° C./min. Later, a preservative was added and the mixture was stirred again at 150 rpm for 5 min. Finally, the corresponding fabric softener compositions were discharged.

TABLE 1

Fabric Softener compositions (percentages referred to active matter)

| | Invention | | | | Comparative Ex. | | | |
|---|---|---|---|---|---|---|---|---|
| | 1 | 2 | 3 | 4 | A | B | C | D |
| Esterquat[1] | 8.00 | 8.00 | 8.00 | 8.00 | 8.00 | 8.00 | 8.00 | 8.00 |
| Ex. 1 | 0.15 | — | — | — | — | — | — | — |
| Ex. 2 | — | 0.15 | — | — | — | — | — | — |
| Ex. 3 | — | — | 0.15 | — | — | — | — | — |
| Ex. 4 | — | — | — | 0.15 | — | — | — | — |
| Example 1 of WO-A-2004047788[2] | — | — | — | — | — | 0.15 | — | — |
| Perfume[3] | 0.85 | 0.85 | 0.85 | 0.85 | 1.00 | 0.85 | 0.85 | 0.85 |
| Decanal | — | — | — | — | — | — | 0.15 | — |
| Undec-10-enal | — | — | — | — | — | — | — | 0.15 |
| Preservative | q.s. | q.s. | q.s. | q.s. | q.s. | q.s. | q.s. | q.s. |
| Deionized water | Up to 100 | Up to 100 | Up to 100 | Up to 100 | Up to 100 | Up to 100 | Up to 100 | Up to 100 |

[1] TETRANYL ® L1/90S (Di-alkyl ester of triethanol ammonium methyl sulphate) available from KAO Chemicals Europe
[2] Example 1 of WO-A-2004047788 (condensation of di-fatty amido amine (Varisoft 510) with decyl aldehyde)
[3] Perfume FPEJ-37190-H-DPG available from KAO Chemicals Europe 32 100% cotton towels (1600 g) were pre-scoured in a domestic washing machine (MIELE Novotronic W 840) using 2 washing/rinsing cycles, the first one at 90° C. and the second one at 60° C., with a commercially available detergent (product name: Ariel, manufactured by Procter & Gamble) at a dosage of 2.68% by weight with respect the weight of the towels for each washing cycles. In both washing/rinsing cycles water of controlled hardness (20° f., French degrees) was used.

16 of the pre-scoured towels (800 g) were washed in the same washing machine with the same detergent at a dosage of 2.68% by weight with respect the weight of the towels at 60° C. During a standard rinsing cycle, the compositions of Table 1 were applied on the towels. In both the washing and the rinsing cycle water of controlled hardness (20° f., French degrees) was used. The softener compositions were added at a dosage of 0.2% by weight with respect the weight of the towels.

Treated towels were smelled by an expert panel of 6 panelists to assess the perfume intensity, both on wet and on dry towels, by means of a triangular test comparing towels treated with comparative examples B-D or compositions 1-4 against towels treated with comparative experiment A (only containing perfume). Triangular test was carried out according to international standard ISO 6658:1985 (Section 6.2.3), so for each pair of products under comparison, 6 different combinations to be evaluated were presented.

On dry towels assessment was carried out after 24 h, 3 days and 7 days after they had been treated with the fabric softener compositions. During all test period towels were stored under controlled temperature and humidity conditions (20° C., 60% RH).

Results of sensorial perfume intensity assessment are given in Table 2.

TABLE 2

Scores to higher perfume intensity (number of positive answers from a total of 36)

| | Wet | 24 h | 3 days | 7 days |
|---|---|---|---|---|
| 1 vs A | 24 | 23 | 20 | 21 |
| 2 vs A | 25 | 32 | 34 | 32 |
| 3 vs A | 29 | 22 | 23 | 27 |
| 4 vs A | 34 | 30 | 35 | 26 |
| B vs A | 22 | 6 | 8 | 17 |
| C vs A | 30 | 5 | 3 | 0 |
| D vs A | 34 | 17 | 12 | 9 |
| 1 vs B | 12 | 17 | 26 | 32 |
| 2 vs B | 9 | 15 | 23 | 28 |
| 1 vs C | 1 | 5 | 28 | 34 |
| 2 vs C | 0 | 3 | 26 | 30 |
| 3 vs D | 1 | 8 | 22 | 29 |
| 4 vs D | 5 | 11 | 25 | 32 |
| 2 vs 1 | 7 | 11 | 26 | 31 |
| 4 vs 3 | 14 | 17 | 28 | 26 |

Compositions 1-4 show a statistically significant perfume intensity enhancement in wet conditions and also a statistically significant enhancement of the odour longevity (substantivity) with respect to the composition containing only perfume (composition A).

On the other hand, compositions B-D only show a statistically significant perfume intensity enhancement in wet conditions with respect to the composition containing only perfume (composition A).

Additionally, after comparing the results of compositions 1-2 with the result of composition B, it can be concluded that a significant enhancement on the odour longevity (substantivity) is observed when using the compounds according to the invention in comparison with known fragrance precursors.

Furthermore, after comparing the results of compositions 1-4 with the result of compositions C and D, it can be concluded that a significant enhancement on the odour longevity (substantivity) is observed when using the compounds according to the invention in comparison with free aldehydes.

Finally, when comparing the results of composition 1 and composition 2, and the results of composition 3 and composition 4, it can be seen that in general, better results with regard to odour longevity (substantivity) are obtained with alkoxylated amines than with alkoxylated esteramines.

Furthermore, the compound according to the invention has a positive effect to the deposition of the perfume on the fibers. Fragrant compounds included in the perfume tend to be dissipated with time. The compound according to the invention, not only helps to enhance the odour longevity (substantivity) of the perfume, but also helps to enhance the initial intensity in wet conditions, just when the perfume has been deposited on the fibers.

This has been corroborated by SPME (Solid Phase Micro-Extraction) GC/MS (Gas Cromatography/Mass Spectrometry).

Compositions 1 and 3 and compositions 2 and 4 were analyzed by triplicate. For each analyzed sample total area of chromatogram was quantified. Additionally, the area of chromatogram due to the compound according to the invention was quantified and subtracted to the total area of chromatogram. Finally, the % of area increase related to composition A was calculated. Results (average of compositions 1 and 3 and average of compositions 2 and 4) are summarized in Table 3.

TABLE 3

| % of total area increase respect to composition A | |
|---|---|
| | Wet |
| Alkoxylated esteramine | 12.3 |
| Alkoxylated amine | 15.3 |

The invention claimed is:

1. A compound of the following formula I:

$$X—CR_1R_2R_3 \quad (I)$$

wherein
R$_1$ is an organic moiety having 6 to 24 carbon atoms;
R$_2$ is H or an organic moiety having 6 to 24 carbon atoms;
R$_3$ is X or OH;
X is a moiety of the following formula II:

or an ammonium or C$_1$-C$_4$ alkyl ammonium salt of the moiety of formula II;

wherein
x is 0 or 1;
y is 0 or 1;
z is 0 or 1;
m is a number from 2 to 10;
n is a number from 0 to 10;
o is a number from 0 to 10;
R$_4$ is H or a C$_1$-C$_4$ alkyl group;
R$_5$ is a C$_6$-C$_{22}$ alkyl or alkenyl group or, if n or o is at least 1, a C$_7$-C$_{23}$ acyl group;
R$_6$ is H or R$_5$;
R$_7$ is a C$_1$-C$_4$ alkylene group.

2. The compound according to claim 1, which is obtainable by reacting X—H, wherein X is defined as in claim 1, with a compound of the formula R$_1$COR$_2$, wherein R$_1$ and R$_2$ are defined as in claim 1, wherein said compound of the formula R$_1$COR$_2$ has a molecular weight of less than 300 g/mol.

3. The compound according to claim 2, wherein the compound of the formula R$_1$COR$_2$ is an aliphatic aldehyde or ketone, a cycloaliphatic aldehyde or ketone, an acyclic terpene aldehyde or ketone, a cyclic terpene aldehyde or ketone, an aromatic aldehyde or ketone, or a phenol aldehyde or ketone.

4. The compound according to claim 2 or 3, wherein the compound of the formula R$_1$COR$_2$ is one of the following compounds: phenylacetaldehyde, p-methyl phenylacetaldehyde, p-isopropyl phenylacetaldehyde, methylnonyl acetaldehyde, phenylpropanal, 3-(4-t-butylphenyl)-2-methyl propanal, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methylpropanal, 3-(4-ethylphenyl)-2,2-dimethylpropanal, phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal (melonal), 2,6-dimethylpropanal, 2,4-heptadienal, octanal, 2-octenal, 3,7-dimethyloctanal, 3,7-dimethyl-2,6-octadien-1-al, 3,7-dimethyl-1,6-octadien-3-al, 3,7-dimethyl-6-octenal, 3,7-dimethyl-7-hydroxyoctan-1-al, nonanal, 6-nonenal, 2,4-nonadienal, 2,6-nonadienal, decanal, 2-methyl decanal, 4-decenal, 9-decenal, 2,4-decadienal, undecanal, 2-methyldecanal, 2-methylundecanal, 2,6,10-trimethyl-9-undecenal, undec-10-enyl aldehyde, undec-8-enanal, dodecanal, tridecanal, tetradecanal, anisaldehyde, bourgenonal, cinnamic aldehyde, a-amylcinnam-aldehyde, a-hexyl cinnamaldehyde, methoxy cinnamaldehyde, citronellal, hydroxy-citronellal, isocyclocitral, citronellyl oxyacet-aldehyde, cortexaldehyde, cumminic aldehyde, cyclamem aldehyde, florhydral, heliotropin, hydrotropic aldehyde, lilial, vanillin, ethyl vanillin, benzaldehyde, p-methyl benzaldehyde, 3,4-dimethoxybenzaldehyde, 3- and 4-(4-hydroxy-4-methyl-pentyl)-3-cyclohexene-1-caroxaldehyde, 2,4-dimethyl-3-cyclohexene-1-carboxaldehyde, 1-methyl-3-4-methylpentyl-3-cyclohexencarboxaldehyde, and p-methylphenoxyacetaldehyde; a-damascone, b-damascone, d-damascone, b-damascenone, muscone, 6,7-dihydro-1,1,2,3,3-pentamethyl-4(5H)-indanone, cashmeran, cis-jasmone, dihydrojasmone, methyl dihydrojasmonate, a-ionone, b-ionone, dihydro-b-ionone, g-methyl ionone, a-iso-methyl ionone, 4-(3,4-methylenedioxyphenyl)butan-2-one, 4-(4-hydroxyphenyl)butan-2-one, methyl b-naphthyl ketone, methyl cedryl ketone, 6-acetyl-1,1,2,4,4,7-hexamethyltetralin (tonalid), 1-carvone, 5-cyclohexadecen-1-one, acetophenone, decatone, 2-[2-(4-methyl-3-cyclohexenyl-1-yl)propyl]cyclopentan-2-one, 2-sec-butylcyclohexanone, b-dihydro ionone, allyl ionone, a-irone, a-cetone, a-irisone, acetanisole, geranyl acetate, 1-(2-methil-5-isopropyl-2-cyclohexenyl)-1-propanone, acetyl diisoamylene, methyl cyclocitrone, 4-t- pentyl cyclohexanone, p-t-butylciclohexanone, o-t-butylcyclohexanone, ethyl amyl ketone, ethyl pentyl ketone, menthone, methyl-7,3-dihydro-2H-1,5-benzodioxepine-3-one, fenchone, methyl naphthyl ketone, propyl naphthyl ketone or methyl hydroxynaphthyl ketone.

5. The compound of claim 1, wherein m is a number from 3 to 8.

6. The compound of claim 1, wherein $R_4$ is H and $R_6$ is $R_5$.

7. The compound of claim 1, wherein x, y, and z are each 1, $R_7$ is an ethylene group, and $R_5$ is a $C_9$-$C_{19}$ acyl group.

8. The compound of claim 1, wherein the sum of m, n, and o is in the range of 10 to 20.

9. The compound of claim 1, wherein x, y, z, and n are each 0, and $R_5$ is a $C_6$-$C_{22}$ alkyl or alkenyl group.

10. The compound of claim 9, wherein o is 0, and $R_6$ is $R_5$.

11. The compound of claim 9, wherein o is a number from 2 to 10, and $R_6$ is H.

12. A composition comprising a mixture of at least two compounds of formula I as defined claim 1, in an aqueous solution.

13. A hair conditioner, comprising a hair conditioning compound and a compound as set forth in claim 1.

14. A fabric softener, comprising a fabric softening compound and a compound as set forth in claim 1.

* * * * *